United States Patent [19]
Chang et al.

[11] Patent Number: 4,750,035
[45] Date of Patent: Jun. 7, 1988

[54] VIDEO CONTAINER INSPECTION WITH COLLIMATED VIEWING OF PLURAL CONTAINERS

[75] Inventors: Roger Chang, Ft. Lauderdale; Donald Darling, Palm Beach Gardens; Mark Filipowski, Lake Worth; Russell Mortensen, West Palm Beach; Jamie Pereira, North Palm Beach, all of Fla.

[73] Assignee: Inex/Vistech Technologies, Inc., Palm Beach, Fla.

[21] Appl. No.: 906,298

[22] Filed: Sep. 11, 1986

[51] Int. Cl.⁴ .............................................. H04N 7/18
[52] U.S. Cl. ................................... 358/106; 358/101; 250/223 B
[58] Field of Search .................... 21358/101, 106, 107; 201/526; 250/223 B; 356/240, 428, 340, 239; 350/417, 437, 452; 352/86; 353/7, 70; 354/77

[56] References Cited

U.S. PATENT DOCUMENTS

| Re. 28,984 | 9/1976 | Drinkuth et al. | 350/106 |
|---|---|---|---|
| 3,394,263 | 2/1968 | Baker | 250/223 B |
| 3,746,784 | 7/1973 | Van Oosterhaust | 358/106 |
| 3,932,042 | 1/1976 | Faani et al. | 356/240 |
| 3,963,348 | 6/1976 | Nakatani et al. | 250/223 B |
| 4,002,823 | 1/1977 | Van Oosterhout | 358/106 |
| 4,136,930 | 1/1979 | Gomon et al. | 358/106 |
| 4,178,516 | 12/1979 | Brugger | 250/223 B |
| 4,376,951 | 5/1983 | Miyazawa | 358/106 |
| 4,459,023 | 7/1984 | Reich et al. | 356/237 |
| 4,498,081 | 2/1985 | Fukushima et al. | 340/793 |
| 4,498,106 | 2/1985 | Sato et al. | 358/273 |
| 4,589,020 | 5/1986 | Akatsuka | 358/160 |
| 4,606,634 | 8/1986 | Bieringer | 250/223 B |
| 4,608,709 | 8/1986 | Hedler et al. | 250/223 B |
| 4,610,542 | 9/1986 | Ringlien | 250/223 B |

Primary Examiner—James J. Groody
Assistant Examiner—John K. Peng
Attorney, Agent, or Firm—Steele, Gould & Fried

[57] ABSTRACT

A video inspection system with collimated viewing of plural containers has a conveyor for continuously transporting bodies disposed immediately adjacent one another to an inspection zone at which the bodies are backlighted. A video detector for capturing and analyzing a digital image of successive containers views the containers through a preferably fresnel collimating lens disposed between the bodies and the video detector, whereby an elevation view of the bodies is achieved. A data processing device operable to correlate the portions of successive images corresponding to a single body proceeding through the inspection zone analyzes the images and operates a downstream apparatus for segregating the bodies based upon visible features.

16 Claims, 2 Drawing Sheets

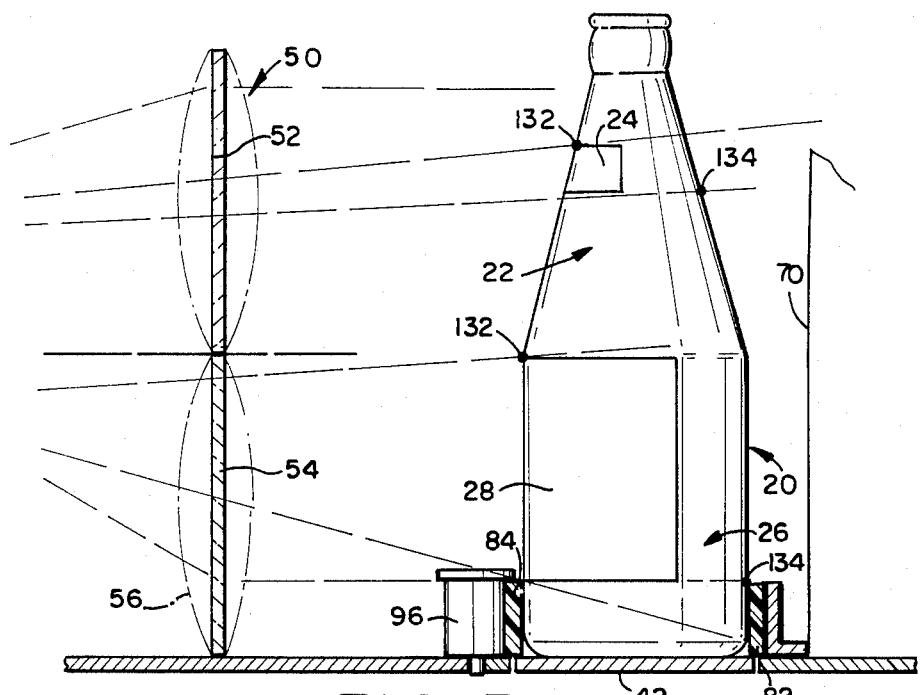
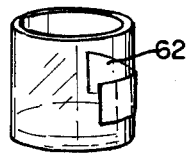
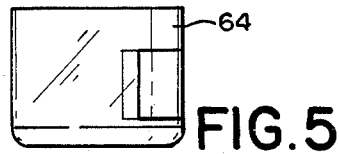
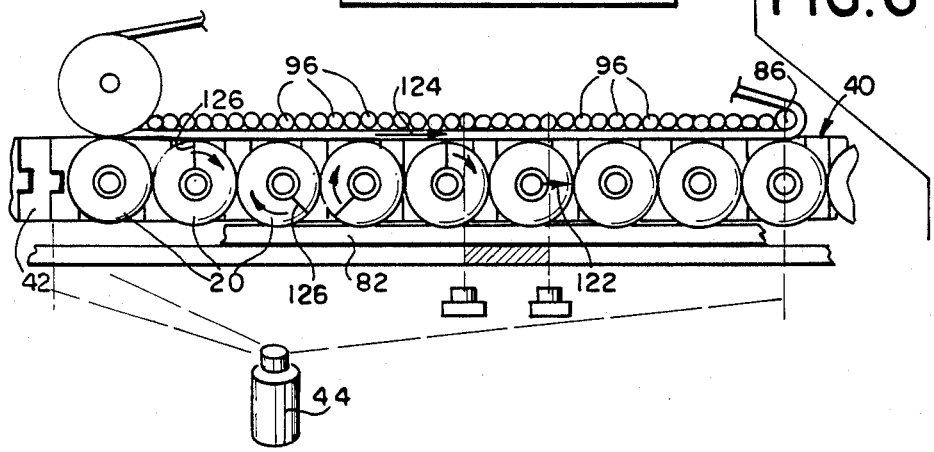

VIDEO CONTAINER INSPECTION WITH COLLIMATED VIEWING OF PLURAL CONTAINERS

BACKGROUND OF THE INVENTION

1. Field of the Invention

This invention relates to the field of sidewall inspection of transparent and translucent bodies, and in particular to a video inspection system in which a succession of collimated elevation views are captured and processed for sorting the bodies, each view showing a plurality of successive bodies.

2. Prior Art

Video sidewall inspection systems are known in various forms in which a video camera is oriented perpendicular to a longitudinal axis of a back-lighted container, to capture and analyze data representing an image of container sidewalls, including both the front sidewall and a rear sidewall. Inasmuch as the view along the sides of the usually-cylindrical container is foreshortened, means are sometimes provided to simultaneously or sequentially secure at least two angularly spaced views around the container to cover the whole surface. Such systems are known to detect defects in the sidewall surfaces, dirt, chips and unusual wear. Examples of sidewall inspection systems can be found, for example, in U.S. Pat. Nos. 3,746,784 and 4,002,823, both to Van Oosterhout, 4,136,930—Gomm et al and 4,376,951—Miyazawa. Insofar as these patents teach processing of data, their disclosures are incorporated.

Video inspection systems take various approaches to the problems of detecting and sorting containers based on their quality, cleanliness, etc. The present invention is concerned with capturing instantaneous views of each successive container from a plurality of angularly-spaced positions. The invention is equally applicable to any of the various forms of analysis, such as those in which areas of contrast are analyzed to detect chips or dirt, or a container is twisted or agitated to produce a relative movement of contrasting foreign material in or on the container.

A video image of a container to be be analyzed is a two dimensional data pattern representing one or more images focused on a plane surface. Prior art inspection systems have attempted to collect an enlarged two dimensional image of container sidewalls by rolling a container in front of a linear or planar detector, but the image is necessarily a two dimensional pattern. The present invention relates to optimizing the data capture in several ways. Using cameras directed at only one inspection field, simultaneous data is captured in which each backlighted container is recorded, rolled ahead to a next successive position within the inspection field and again recorded from the new angular aspect, etc. The data processor of the invention rejects containers for defects in any view, and preferably correlates the images of one container from the successive views to analyze for defect patterns, taking care to appropriately handle gaps in the views occurring when processing leading and trailing containers in a line.

Collection of a two dimensional simultaneous view of a plurality of containers has certain costs and certain benefits. The simultaneous view allows the user to continue to transport containers along a conveyor in front of one recorder station, rather that stopping for recordation of a data image or using spaced stations. In order to accomplish such a feat for a plurality of containers to be recorded simultaneously, the invention provides a large diffuse backlighted area in which the backlighting is sufficiently even to allow a high resolution examination of the image for variations in brightness indicative of dirt, wear or damage. Moreover, a true elevation view is recorded.

Processing an image of an item having more than a trivial depth in the viewing direction presents certain problems of perspective. Prior art systems have attempted to resolve viewing problems by providing extensive optics to provide a substantially perpendicular view of a sidewall for inspection. An example of such a system is found in U.S. Pat. No. 3,932,042-Fanni, et al, in which various lenses and reflectors are used to facilitate recordation of an image of a single bottle from angularly spaced perpendicular directions through the sidewall. A split image technique is employed together with substantially-parabolic reflectors disposed adjacent light sources, in a effort to provide even backlighting and a substantially elevational view. Such optical systems may be effective, but are prone to difficulty in that any sophistication in optics means expensive hardware, and will require a great deal of maintenance to maintain the necessary precision of alignment, cleanliness of elements and the like.

Perspective effects in an image recorded by a video camera viewing a cylindrical container or the like can have a substantial impact on analysis of transparent or translucent bodies. Perspective views are characterized by relatively larger foreground features due to the diverging lines along which the effective point light receptor (i.e., the video camera) views the container. Should either the foreground or background sidewall present an opaque label or other feature that interferes with analysis because the other sidewall cannot be viewed, the divergence of perspective viewing lines rays results in a larger obstruction in perspective viewing than for a true elevation view. The obstructed or obstructing field of the rear sidewall is larger than that of the front sidewall. For example, in order to detect faults in a given area on the front sidewall, it is necessary to ensure that no opacity such as a label appears on a larger area of the rear sidewall that would be traced by diverging rays from the video detector. A perspective view of the container also has the inherent difficulty that certain portions of each sidewall (e.g., near the bottom edge) are not subject to inspection due to their association with portions visible through the sidewall that cannot be inspected due to opacities other than defects.

It is theoretically possible to reduce problems with perspective viewing by providing a very long focal length view of a container being inspected. For example, a telephoto lens viewing the container would effectively view the container from a longer distance, thereby providing less-divergent viewing lines and a more elevational view. This is a theoretical solution to perspective problems, but may not be practical. Telephoto lens optics are expensive and heavy, and can be subject to problems with dirt in a production environment. Furthermore, in order to provide a relatively large field of view, for example to minimize the number of cameras required to cover a field and/or to record simultaneously the image of a number of containers positioned successively on a conveyor, such a telephoto viewing system would either have to be positioned at a substantial distance from the containers being inspected, or would be very heavy and expensive in the optical hardware needed to ensure good resolution, good light transmission, etc.

The present invention provides a true elevation view of a plurality of containers simultaneously, preferably using only one upper and one lower video camera, and collimating the image of the successive containers. The collimating is preferably accomplished using a fresnel lens, whereby the weight and expense of the collimator are minimized. A fresnel lens in this application tends to disrupt the image of the container as it appears to the eye due to the ridged nature of a fresnel lens. However, this apparent degradation of the image is substantially outweighted by the benefits inherent in providing a true elevation view of the container. Moreover, lens ridge effects are subject to removal by analysis techniques in which the brightness of pixels is statistically analyzed.

Together with a means for continuously rolling bottles moving along the container, the invention records upper and lower images of three successive containers, and correlates the data from these images to analyze and segregate containers for any defects such as dirt, wear, bird's wings, etc. The invention is accordingly quite effective yet the expense of providing a true elevation view is minimized by the relatively inexpensive optics and the need for only one or two video cameras successively recording images of a series of adjacent containers.

SUMMARY OF THE INVENTION

It is an object of the invention to provide an inexpensive and dependable sidewall inspection device operative to capture and analyze angularly-spaced elevation views of a plurality of containers.

It is also an object of the invention to provide an effective container inspection system in which a minimum number of video cameras and a minimum expense in optics are required, yet which is capable of capturing data at high resolution for sophisticated analysis.

It is another object of the invention to provide an evenly-backlighted true elevation view of containers being inspected, to thereby maximize the area of the sidewalls subject to analysis.

It is still another object of the invention to provide sequential views of successive conveyed containers without stopping the containers, by securely rolling the containers on a moving conveyor, using an apparatus that does not interfere with view.

These and other objects are accomplished by a video inspection system with collimated viewing of plural containers having a conveyor for continuously transporting bodies disposed immediately adjacent one another to an inspection zone at which the bodies are backlighted. A video detector for capturing a digital brightness data image of successive containers views the containers through a preferably fresnel collimating lens disposed between the bodies and the video detector, whereby an elevation view of the bodies is achieved. A data processing device operable to correlate and analyze those portions of successive images corresponding to a single body proceeding through the inspection zone analyzes the images and operates a downstream apparatus for segregating the bodies based upon visible features.

BRIEF DESCRIPTION OF THE DRAWINGS

There are shown in the drawings the embodiments that are presently preferred. It should be understood, however, that the invention is not limited to the precise arrangements and instrumentalities shown in the drawings, wherein:

FIG. 3 is a section view taken along lines 3—3 in FIG. 1.

FIG. 4 is a partial perspective view of a container base.

FIG. 5 is an elevation view of the container base from approximately the same viewpoint.

FIG. 6 is a partially schematic elevation view corresponding to FIG. 1, and showing the particulars of container rotation.

DETAILED DESCRIPTION OF THE PREFERRED EMBODIMENTS

Figure 1:
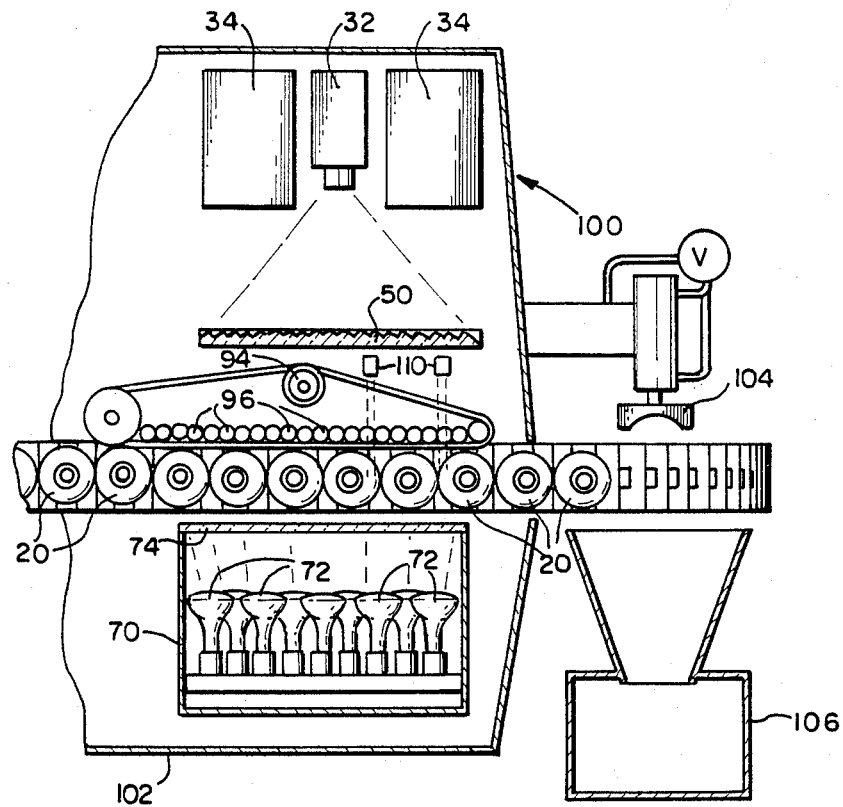
FIG. 1 is an elevation view of the sidewall inspection system of the invention, with the casing shown partially cut away.

With reference to FIG. 1, a plurality of transparent or translucent containers 20 are being carried along a continuously moving conveyor 40 such that the bottles 20 remain positioned immediately adjacent one another. The inspection system as disclosed is intended, for example, to be positioned downstream of a container washing facility in a returnable bottle processing plant or downstream of molding or annealing facilities in a container production plant. Analysis and segregation of the containers can be for container type, chips, dirt or defects, wear patterns, remaining wash water, etc. The invention relates primarily to means for capturing data, the analysis of which can be by techniques otherwise known. At the sidewall inspection area, one or more video cameras 32 are disposed to record a video image representing the sidewalls of successive containers 20, backlighted using lamps 72, directed against a diffuse light transmissive panel 74 disposed immediately opposite the bottles from the video camera 32.

The invention is discussed and illustrated in an embodiment directed to transparent glass bottles such as those in use for soft drinks. It should be understood that the invention is equally applicable to other articles subject to inspection, for example translucent articles, plastic articles and other types of articles having a generally cylindrical shape.

The containers (e.g., soft drink bottles) according to the invention are processed without the need to stop or to separate the containers by any distance whatsoever. The invention also avoids use of a plurality of spaced or angled video cameras, or optical image splitters to achieve angularly spaced views of the containers 20. Instead, the containers 20 are fed in a solid line along a continuously moving conveyor 40 and in the area of sidewall inspection are caused to roll while moving along the conveyor between a driven belt on one side of the conveyor and a stationary rail on an opposite side of the conveyor. Rub rail 82 remains stationary. Moving belt 84 on the other side of the conveyor engages the bottom edge of the bottle and engages the bottles against the stationary side rail 82. The belt 84 is moved continuously, as is the conveyor 40. Preferably, belt 84 moves at precisely twice the speed of conveyor 40, such that the average speed of each container remains the same as the transport conveyor 40, although the bottles are rolled in this area.

Belt 84 and rail 82 preferably engage at the lowermost edge of the containers, for example at the lowermost edge of a right cylindrical section of the containers. This keeps the belt from obscuring view of the container. The close proximity of the containers helps to keep them upright. Supportive rails can be provided in the rolling area, for example at the container neck.

In another embodiment of the invention (not shown), the rub rail 82 is replaced by a second driven belt. The second belt is driven at a different speed than belt 84, thereby rotating the containers inthe inspection area. Complete control of container rotation is possible using two driven belts, preferably in order to present a plurality of equally-angularly spaced views with minimum danger by imparting a minimum of rotational force to the containers.

Views including a large number of containers and a small rotation from container to container are possible and may increase the possible line speed. By using two belts 84 on opposite sides running at relative speeds to achieve a 60 degree rotation within the linear travel of one container diameter, each container will present 6 equally spaced views within the space of six containers. Accordingly, frames of six containers results in a fully redundant correlated view for each, in which the whole circumference can be examined in front sidewall view.

Whether three or six containers are included in the inspection plurality of the rolling containers (e.g., bottles) in the inspection zone are exposed to the video camera and are viewed simultaneously. Preferably, a sidewall view of three or more bottles or like containers is recorded every time any one bottle passes a predetermined location defined, for example, by photocells 110. The photocells initiate a sequence leading to recordation of a digital grey level image to be analyzed. The photocells activate flash lamps 72, preferably a plurality of evenly spaced strobe lamps, and then initiate recording of an image in video camera 32. Video camera 32 is preferably a charged coupled device (CCD), of the type employed in many industrial image processing systems. To avoid jitter, capturing of the image is preferably synched to container position rather than only to a free running repetitive synch. Camera 32 is connected to power supply and control elements 34, including one or more data processors for controlling image capture and analysis, and also for enabling a downstream kicker mechanism 104, operative to sort bottles based upon the sensed conditions thereof.

Figure 2:
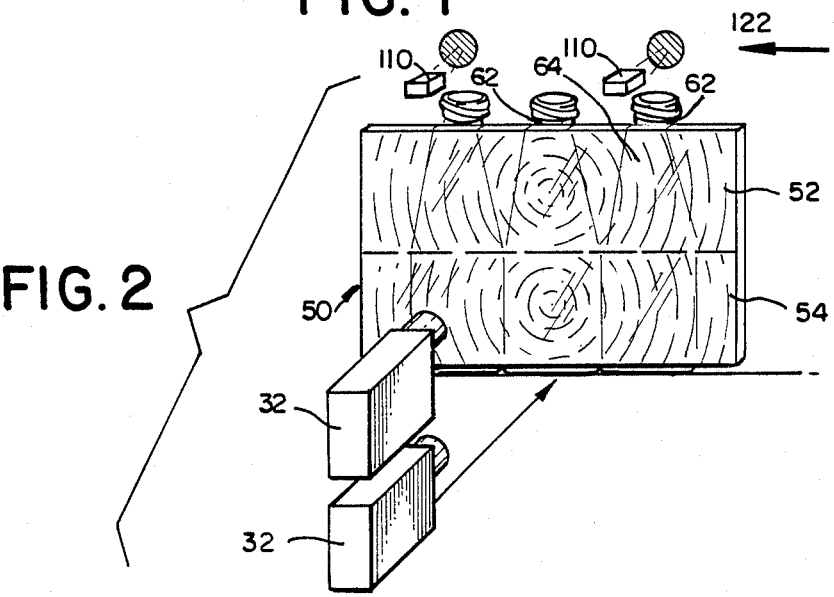
FIG. 2 is a schematic perspective view illustrating collimation of the container images using a fresnel collimator.

FIG. 2 illustrates the effect of collimator 50, which is placed between containers 20 and video cameras 32. The collimator 50 is spaced from cameras 32 at a distance equal to the focal length of collimator 50, such that parallel rays of light striking perpendicularly against the backside of collimator 50 will be refracted by the collimator and focused at the focal point occupied by camera 32. In this manner, camera 32 records a precise elevation view of the containers, rather than a perspective view. A collimated multi-container image is recorded every time any container passes a photocell 110, moving along the transport direction as indicated by arrow 122 in FIG. 2.

Collimator focal length is preferable relatively short, to thereby limit the overall size of the inspection system. A focal length of about 30 cm to 50 cm (12 to 20 inches) is appropriate in the typical production facility.

Collimator 50 is preferably a fresnel lens, i.e., a lens in which the theoretical contour 56 of a collimating lens, indicated in dash dot lines in FIG. 3, is segmented, and the individual refracting surfaces brought closer by shortening the segments. A means for making an annular segment version of such a lens is shown in U.S. Pat. No. 2,441,747—Beshgetoor. Other segmentations are also possible, such as the mosaic segmentation of U.S. Pat. No. 3,053,144—Harries, et al. Use of a fresnel lens avoids the large amount of glass that would be required to define a smooth lens according to the theoretical contour 56, however, the fresnel lens has visible ridges, corresponding to the discrete incremental refracting surfaces.

According to the invention, an upper and lower camera 32 record upper and lower views of the plurality of containers 20 in the inspection zone. An overall elevation view 64 is recorded rather that a perspective view 62. FIG. 3 shows the difference between an elevation view and perspective view by means of comparison of the diverging lines and parallel lines between the video camera (not shown to the left of collimator 50) and the container. Collimated viewing lines run horizontally and are parallel. Perspective viewing lines diverge. An upper label 24 or lower label 28 on bottle 26 will effectively preclude video inspection of an area somewhat larger than the actual length of labels 24, 28 in their vertical dimension. More particularly, label 24 precludes any dependable analysis of the area below a perspective view ray passing through point 132, defining the upper edge of the upper label 24 and point 134, defining the lower edge of the label as rotated. However, a perspective line through point 134 at the front, in fact passes through the bottom edge as shown. Therefore, label 28 precludes a view somewhat above the label top edge.

Perspective effects cause labels and the like to indirectly obscure substantially larger areas than they directly obscure. Moreover, if efforts are made to reduce the overall size of the inspection device by increasing the field of view and/or bringing the camera closer to the container, perspective effects are aggravated. According to the invention, by collimating the image and thereby providing an elevation view, a substantially larger portion of the container is subject to inspection. The practical effect of the difference is seen in comparing FIGS. 4 and 5. FIG. 4 shows a lower end perspective view in which a label obviously occupies a relatively larger area in the image than the actual height of the label. Elevation view 64, however, limits the obstruction of the label to its vertical extension in a corresponding collimated elevation view.

FIG. 6 illustrates particulars of a preferred embodiment for rotating the containers 20 on their axes as they are carried along the conveyor 40. Conveyor 40 is an endless belt comprised of a plurality of serially connected links 42. The containers 20 rest on the links and are carried along the transport path at a conveyor link velocity, indicated by arrow 122. As the containers are passed by idling star wheel 88, they bear against stationary rub rail 82 on one side and are driven on the opposite side by roller drive belt 84 at a speed greater than that of conveyor 40, to thereby roll the bottles along stationary rail 82. A theoretical identification mark 126 is shown on the bottles in FIG. 6 to indicate the extent to which the bottles have rolled along. Belt 84 is preferably driven by capstan 86 at a speed directly related to conveyor 40, for example by mechanically gearing capstan 86 to the same drive motor 44 driving the conveyor 40. Accordingly, the speed of conveyor 40 can be varied without losing the relationship between velocity 124 of belt 84 and velocity 122 of conveyor 40. The bottles will rotate a full circumference as they move along conveyor linearly by a distance equal to their diameter times pi, i.e., in the linear space of 3.14 bottles. According to the invention, the image of three successive bottles in the rolling zone is captured every time a bottle passes a point defined by one of the photocell detectors. Inasmuch as each bottle rolls a full circumference in a distance nearly equal to three bottle diameters, and successive views of each bottle show the bottle from an angularly spaced view of about 120 degrees, the device is effective to achieve three almost perfectly angularly spaced views of each bottle, without undue mechanical complications that could interfere with smooth flow of bottles along the line.

In another preferred embodiment, the bottles are rotated 60 degrees per linear advance of one diameter, by means of drive belts 84 on both sides of the conveyor. The average speed of the belts vary in speed from one another by the desired amount of rotation. For 60 degree rotation, 6 bottles can be viewed at once. Alternatively, additional cameras can be used to collect an image of 3 bottles per camera station, at the same resolution as above. Preferably, the additional cameras are likewise provided with photoeyes for triggering, video processors for data acquisition and control functions, etc.

The stability of the overall conveying mechanism is affected by the rotation imparted to the bottles. By decreasing rotation to 60 degrees per diameter the possibility of damage is correspondingly decreased.

The respective images, more particularly shown in FIG. 2, can be correlated to associate those portions of successive images relating to each successive container. As each container progresses along the transport path 122, it appears successively one container position further to the left for each view as shown in FIG. 2. Data processing hardware disposed in control and electronics packaging 34 can include data storage buffers operable to store and correlate the portions of successive images that belong to the same container. For example, even if the level of wear in any one image might be acceptable, the images can be compared such that uneven wear patterns or the like may be grounds for rejection. Images are stored and processed in digital format, each pixel being encoded as a brightness or grey level in a range, for example, of one part in a range of 256, for an image filed of 256×256 pixels. The pixel data can be acquired by sampling and digitizing a video signal from a CCD camera or other video signal source. The actual processing particulars by which the processor discriminates among containers by type or for defects are subject to many variations. Known processing techniques could include image analysis for detecting edges of the containers, masking the edges and scanning the remainder for points of contrast characteristic of cracks, chips, dirt, etc. Data processing according to any known technique is facilitated by the device of the invention, due to the improved capture of data at the outset.

Analysis of each bottle is completed prior to its passing a sorting mechanism such as reject kicker 104. The processor counts passing containers and controls the sorting mechanism, possible discarding a container into hopper 106 as it passes the kicker. The data processor has at least a full six views of the container, three for the top and three for the bottom, at relatively equally angularly spaced points around the bottle, which images can be compared and analyzed for occurrences of chips, dirt, wear, bird's wings, excess moisture or the like. For 60 degrees spacing, twelve views are available. The device can also include rim and/or base analysis equipment.

The invention having been disclosed, a number of additional variations will now occur to persons skilled in the art. Reference should be made to the appended claims rather than the foregoing specification as indicating the true scope of the invention.

What is claimed is:

1. An inspection system for transparent and translucent bodies having a width and depth, the system comprising:
   a conveyor for transporting the bodies to an inspection zone;
   a video detector and processor operable to record and analyze data corresponding to an image of each successive body, the data being at least one two dimensional array of pixels representing light and dark levels at spaced points in the image of the body; and,
   a collimating lens disposed between the body and the video detector, the collimating lens being a segmented fresnel lens having a plurality of discrete annular surfaces oriented to refract parallel light rays from the body to the video detector, the discrete surfaces defining arcs around at least one axis of symmetry corresponding to at least one viewing axis of the video detector, the collimating lens having a focal length, the video detector being spaced from the collimating lens by the focal length, whereby the image analyzed is an elevation view of the body.

2. The inspection system of claim 1, wherein the video detector comprises at least two video cameras disposed adjacent one another and the collimating lens is a composite lens having at least two collimating sections aligned coaxially with each of said video cameras.

3. The system of claim 1, wherein the fresnel lens defines arcs around two axes of symmetry corresponding to an upper viewing axis for an upper video detector and a lower viewing axis for a lower video detector.

4. The inspection system of claim 1, further comprising diffuse backlighting means disposed on an opposite side of the body from the video detector.

5. The system of claim 4, wherein the diffuse backlighting means comprises a plurality of spaced lamps and a translucent panel covering the lamps.

6. The system of claim 5, wherein the lamps are strobe flash lamps evenly spaced in two dimensions and disposed at a distance behind the translucent panel.

7. An inspection system for transparent and translucent bodies having a width and depth, the system comprising:
   a conveyor for transporting the bodies to an inspection zone;
   a video detector and processor operable to record and analyze data corresponding to an image of each successive body, the data being at least one two dimensional array of pixels representing light and dark levels at spaced points in the image of the body; and,
   a fresnel collimating lens disposed between the body and the video detector, the fresnel collimating lens having a plurality of discrete annular surfaces defining arcs around at least one axis of symmetry corresponding to at least one viewing axis of the video detector, the collimating lens having a focal length, the video detector being spaced from the collimating lens by the focal length, whereby the image analyzed is an elevation view of the body, and wherein the collimating lens encompasses a view of a plurality of bodies disposed adjacent one another on the conveyor.

8. A container inspection system for front and back sidewalls of light transmissive bodies, comprising:

a conveyor operable to continuously transport the bodies in succession to an inspection zone and to rotate the bodies at the inspection zone during transport;

means for backlighting the bodies;

at least one video camera operable to record at least one instantaneous image including a plurality of adjacent ones of the bodies, the video camera being synchronized to record said image for each of the bodies passing through the inspection zone;

a collimating lens disposed between the video camera and said bodies and spaced from the video camera by a focal length of the collimating lens, the collimating lens producing an elevation view of the bodies;

data processing means operable to analyze the image and to correlate sections of successive images showing views of successive ones of the bodies; and, means for segregating the bodies responsive to the data processing means.

9. The system of claim 8, wherein the collimating lens is a segmented lens having a plurality of discrete surfaces oriented to refract parallel light rays from the body to the video detector.

10. The system of claim 8, wherein the video detector comprises at least two video cameras disposed adjacent one another and the collimating lens is a composite lens having collimating sections aligned to each of the video cameras.

11. The system of claim 8, further comprising a photocell operable to trigger recordation of the instantaneous image by the video camera, the photocell triggering the camera upon each successive body reaching a predetermined location along the conveyor.

12. The system of claim 11, comprising at least two photocells operable to detect bodies arriving at least two predetermined locations, said data processing means being responsive to said photocells to determine presence of a plurality of the bodies at successive locations in an inspection area, whereby correct operation for leading and trailing bodies in a line of bodies is accomplished.

13. The system of claim 11, wherein the lens is a fresnel lens having discrete annular surfaces defining arcs around at least one axis of symmetry corresponding to at least one viewing axis of the video detector.

14. The system of claim 8, wherein the bodies are generally cylindrical and the conveyor comprises conveying means with a body-turning carrying the device bodies to the inspection zone at a transport velocity, a means adjacent the conveying means frictionally engaging the bodies along one side of the conveyor and a body-rolling belt frictionally engaging the bodies along an opposite side of the conveyor, the body rolling belt being driven at greater than the transport velocity and said means being relatively more stationary, whereby the bodies are rolled while moving at the transport velocity.

15. The system of claim 14, wherein the conveying means is an endless belt supporting the bodies from below and the body turning device engages the bodies immediately adjacent a lower edge of the bodies.

16. The system of claim 14, wherein the instantaneous image includes at least three successive bodies along the stationary rail.

* * * * *